(12) United States Patent
Qureshi et al.

(10) Patent No.: US 7,543,586 B2
(45) Date of Patent: Jun. 9, 2009

(54) SYSTEM AND METHOD FOR TRANSCUTANEOUS MONITORING OF ENDOTRACHEAL TUBE PLACEMENT

(75) Inventors: Adnan I. Qureshi, Orange, NJ (US); Afshin A. Divani, Orange, NJ (US)

(73) Assignee: University of Medicine & Denistry of New Jersey, Somerset, NJ (US)

( * ) Notice: Subject to any disclaimer, the term of this patent is extended or adjusted under 35 U.S.C. 154(b) by 309 days.

(21) Appl. No.: 11/303,861

(22) Filed: Dec. 16, 2005

(65) Prior Publication Data

US 2007/0137652 A1 Jun. 21, 2007

(51) Int. Cl.
*A61M 16/00* (2006.01)

(52) U.S. Cl. .............. 128/207.14; 128/207.15; 128/200.26

(58) Field of Classification Search ............ 128/207.14, 128/200.26, 207.15, 207.16
See application file for complete search history.

(56) References Cited

U.S. PATENT DOCUMENTS

| | | | | |
|---|---|---|---|---|
| 4,431,005 A | * | 2/1984 | McCormick | 600/433 |
| 4,960,122 A | * | 10/1990 | Mizus | 128/207.14 |
| 4,976,261 A | | 12/1990 | Gluck et al. | |
| 5,499,625 A | * | 3/1996 | Frass et al. | 128/207.15 |
| 6,161,537 A | | 12/2000 | Gravenstein et al. | |
| 6,173,199 B1 | | 1/2001 | Gabriel | |
| 6,216,696 B1 | * | 4/2001 | van den Berg | 128/207.14 |
| 6,651,665 B1 | | 11/2003 | Sellers et al. | |
| 6,701,918 B2 | | 3/2004 | Fariss et al. | |
| 6,715,491 B2 | | 4/2004 | Cooper et al. | |

* cited by examiner

*Primary Examiner*—Steven O Douglas
(74) *Attorney, Agent, or Firm*—Klauber & Jackson LLC

(57) ABSTRACT

The present invention relates to a tracheal intubation device and method for placing an endotracheal tube within a patient's trachea. More particularly, the endotracheal tube includes primary and secondary cuffs, in the form of inflatable balloons. A stillette is positioned within the endotracheal tube. The tracheal intubation device includes a guiding mechanism for guiding the stillette and the endotracheal tube within a patent's body. The guiding mechanism is positioned external to a patient and sized and shaped so as to transmit a signal and to receive a signal indicating the location of the stillette in a patient's body. After the endotracheal tube is positioned in the oropharynx, inflating the secondary cuff urges the endotracheal tube toward the trachea of a patient.

17 Claims, 8 Drawing Sheets

US 7,543,586 B2

SYSTEM AND METHOD FOR TRANSCUTANEOUS MONITORING OF ENDOTRACHEAL TUBE PLACEMENT

FIELD OF THE INVENTION

The present invention relates to endotracheal tubes, and more particularly, to a device and method for facilitating the placement of an endotracheal tube within the trachea.

BACKGROUND OF THE INVENTION

Certain medical conditions can cause a patient's airway to become blocked, thereby preventing air from passing to the lungs. A commonly used therapy to treat a blocked airway involves inserting an endotracheal tube into the patient's trachea in order to restore airway patency. The insertion of the endotracheal tube into a patient's trachea is referred to as tracheal intubation.

In a tracheal intubation procedure, the endotracheal tube passes through a patient's mouth, through the larynx, and into the trachea. Once the endotracheal tube passes the larynx, it is difficult to properly align the tube into the trachea, because the inlets of the trachea and the esophagus are very close to each other, and the endotracheal tube is often inadvertently placed into the esophagus. Such misalignment significantly increases operating time and reduces the efficiency of the medical procedure. Such misalignment can also injure a patient by bruising the trachea and the esophagus tissues.

Various methods exist to facilitate the alignment of the endotracheal tube within the trachea. For example, a conventional method used to perform tracheal intubation is by direct laryngoscopy, in which a laryngoscope is used to visualize the patient's airway. In direct laryngoscopy, the laryngoscope is initially inserted into a patient's mouth. The patient's neck is then extended so that the inlet of the trachea can be visualized in order to facilitate the subsequent insertion of the endotracheal tube. Although direct laryngoscopy may be the most commonly used intubation technique, this method is cumbersome and poses a serious risk to patients that have neck injury.

SUMMARY OF THE INVENTION

The shortcomings and disadvantages of the prior art discussed above are overcome by providing an improved tracheal intubation device, which includes a endotracheal tube for insertion into a patient's body. More particularly, the endotracheal tube includes a tubular body, and primary and secondary cuffs attached to the tubular body. The secondary cuff is located proximal to the primary cuff. Both the primary cuff and the secondary cuff are inflatable from a collapsed position to an expanded position. As the secondary cuff inflates, the endotracheal tube is moved in an anterior direction toward the inlet of a patient's trachea. The tracheal intubation device also includes a stillette removably positioned within the tubular body and a guiding mechanism for guiding the stillette and the endotracheal tube within a patent's body. The guiding mechanism is positioned external to a patient and includes an indicator for indicating the location of the stillette. The guiding mechanism is sized and shaped so as to transmit a signal and to receive a signal indicating the location of the stillette in a patient's body.

A method is also disclosed for positioning the endotracheal tube within a patient's body. Initially, the endotracheal tube is inserted in a patient's body until a distal end of the endotracheal tube is positioned adjacent to the junction of the trachea and the esophagus. Then, the endotracheal tube is urged in an anterior direction toward the inlet of the trachea, which can be performed by inflating a secondary cuff on the tube. After the endotracheal tube is pushed toward the inlet of the trachea, the stillette is inserted into the trachea. Once the position of the stillette inside the trachea is confirmed by the guiding mechanism, the endotracheal tube is continually inserted until the distal end of the endotracheal tube is positioned within the trachea.

BRIEF DESCRIPTION OF THE DRAWINGS

For a more complete understanding of the present invention, reference is made to the following Detailed Description of the Invention, considered in conjunction with the accompanying drawings, in which.

DETAILED DESCRIPTION OF THE INVENTION

Figure 1:
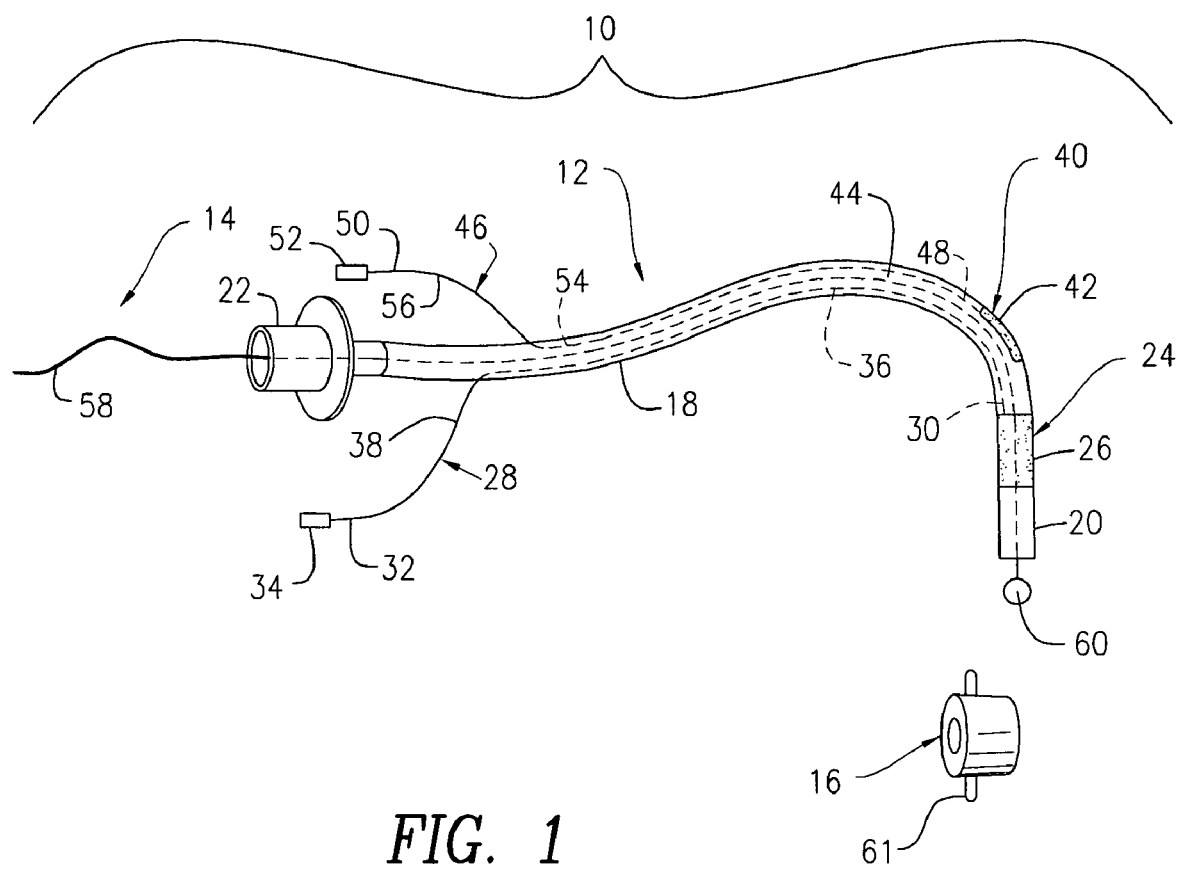
FIG. 1 is a perspective view of a tracheal intubation device according to the present invention, which includes an endotracheal tube with primary and secondary cuffs, having a metal stillette inserted within the endotracheal tube, and an external guide system.

FIG. 1 illustrates a tracheal intubation device 10 that is used to facilitate ventilation in patients that have blocked airways. The tracheal intubation device 10 includes an endotracheal tube 12, a metal stillette 14, and an external guide system 16. The endotracheal tube 12 includes an elongate tubular body 18 that has a distal end 20 and a proximal end 22. The tubular body 18 can be made from any flexible material known in the art, such as plastic, silicon, and tygon.

Figure 2:
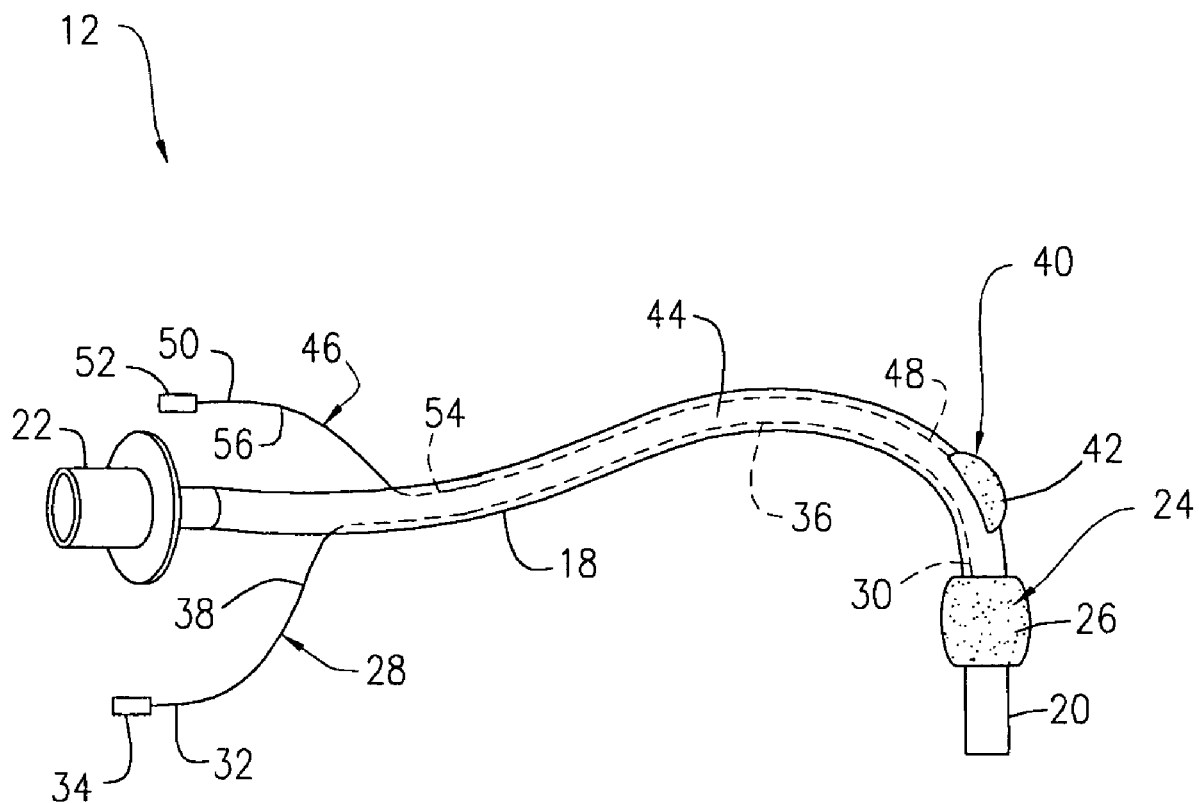
FIG. 2 is a perspective view of the endotracheal tube shown in FIG. 1, which shows the primary and secondary cuffs in expanded configurations.

With reference to FIGS. 1 and 2, the endotracheal tube 12 further includes a primary cuff 24 attached to the tubular body 18 adjacent to the distal end 20 of the tubular body 18. The primary cuff 24 includes a first inflatable balloon 26, which extends about the entire circumference of the tubular body 18. For reasons to be discussed hereinafter, the first balloon 26 is sized and shaped so as to inflate into a fully expanded configuration as shown in FIG. 2 and to deflate into a fully collapsed configuration as shown in FIG. 1.

Referring to FIGS. 1 and 2, a first inflating conduit 28 is provided for receiving air and vacuum. The first inflating conduit 28 has one end 30 connected to the first balloon 26 and an opposite end 32 connected to a luer lock connector 34.

The first inflating conduit 28 extends through an interior passageway 36 within the tubular body 18, and includes an exterior portion 38 extending from the interior passageway 36 adjacent the proximal end 22 of the tubular body 18. The air supplied via the first inflating conduit 28 can be used to inflate the first balloon 26 to its fully expanded configuration as shown in FIG. 2, and the vacuum supplied via the first inflating conduit 28 can be used to deflate the first balloon 26 to its fully collapsed configuration as shown in FIG. 1.

With continued reference to FIGS. 1 and 2, the endotracheal tube 12 is also provided with a secondary cuff 40 positioned at a location proximal to the primary cuff 24. The secondary cuff 40 includes a second inflatable balloon 42, which is attached to the dorsal section 44 of the tubular body 18 and covers approximately half of the circumference of the tubular body 18. For reasons to be discussed hereinafter, the second balloon 42 is sized and shaped so as to inflate into a fully expanded configuration as shown in FIG. 2 and to deflate into a fully collapsed configuration as shown in FIG. 1. A second inflating conduit 46 is provided for receiving air and vacuum. The second inflating conduit 46 has one end 48 connected to the second balloon 42 and an opposite end 50 connected to a luer lock connector 52. The second inflating conduit 46 extends through an interior passageway 54 within the tubular body 18, and includes an exterior portion 56 extending from the interior passageway 54 adjacent the proximal end 22 of the tubular body 18. The air supplied via the second inflating conduit 46 can be used to inflate the second balloon 42 to its fully expanded configuration as shown in FIG. 2, and the vacuum supplied via the second inflating conduit 46 can be used to deflate the second balloon 42 to its fully collapsed configuration as shown in FIG. 1.

Referring to FIG. 1, the metal stillette 14 is shaped so as to be coaxially received within the tubular body 18 of the endotracheal tube 12. The metal stillette 14 has a proximal end 58 and an enlarged spherical distal end 60 that has a diameter of about ¼ inch. The metal stillette 14 is covered with plastic or any other suitable biocompatible coating. The metal stillette 14 has a length in a range of from about 2 to about 2.5 feet and a diameter of about ⅛ inch. It should be understood that the above dimensions for the metal stillette 14 are merely exemplary and that the metal stillette 14 can have other dimensions.

The external guide system 16 (see FIGS. 1 and 3-6) is used to identify the position of the endotracheal tube 12 by identifying the location of the stillette 14, from outside the body using various methods such as, for example, magnetic, electromagnetic, ultrasound, or capacitive sensing. As such, the external guide system 16 comprises an indicator 61 positioned outside the body to detect the position of a stillette. Metal detectors known in the art can be suitably modified for such a purpose. The external guide system 16 could include both a transmitter (not shown) for transmitting a signal and a receiver (not shown) for receiving a signal. A loudspeaker (not shown) and multiple light emitting diodes (LEDs) (not shown) can be provided within the external guide system 16. A simple magnetic finder, like the type used to find studs in walls, i.e., a swiveling magnetic rod, could even be employed for the external guide system 16. The finder could be placed at a patient's throat and the rod would point to the metal stillette 14 when the metal stillette 14 is positioned at the oropharynx.

In order to fully understand the advantages of the tracheal intubation device 10, a brief overview of the throat 62 is discussed below with reference to FIGS. 3-7. The structures of the throat 62 include the oropharynx 64, the trachea 66, and the esophagus 68. The oropharynx 64 is located in the rear of the mouth 70. The trachea 66 and the esophagus 68, which is located dorsal to the trachea 66, are situated below the oropharynx 64.

In operation, prior to inserting the endotracheal tube 12 into a patient's throat 62, the metal stillette 14 is placed within the endotracheal tube 12 such that the distal end 60 protrudes from the distal end 20 of the tubular body 18 and the proximal end 58 protrudes from the proximal end 22 of the tubular body 18. The external guide system 16 is positioned at the anterior side of the patient's neck. The external guide system 16 can be retained in place by a strap around a patient's neck and can be placed at a 45 degree angle such that the transmitted and received signal of the external guide system 16 can be passed through the trachea 66 without interacting with the esophagus 68.

Figure 3:
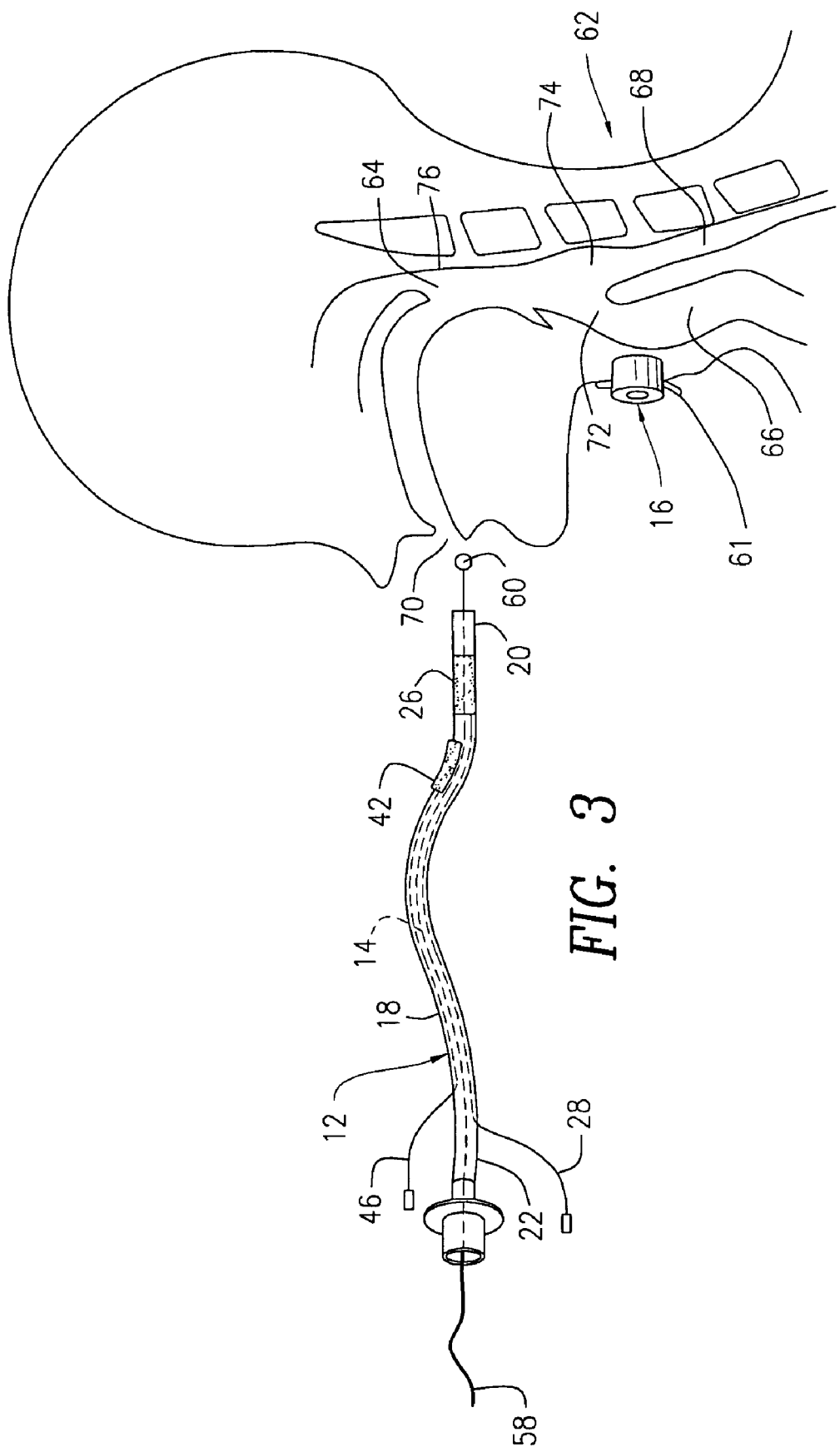
FIG. 3 is a schematic view of a patient's upper airway and the tracheal intubation device shown in FIG. 1, which shows the endotracheal tube and the metal stillette aligned with a patient's mouth, and the external guide system attached to a patient's neck.
Figure 4:
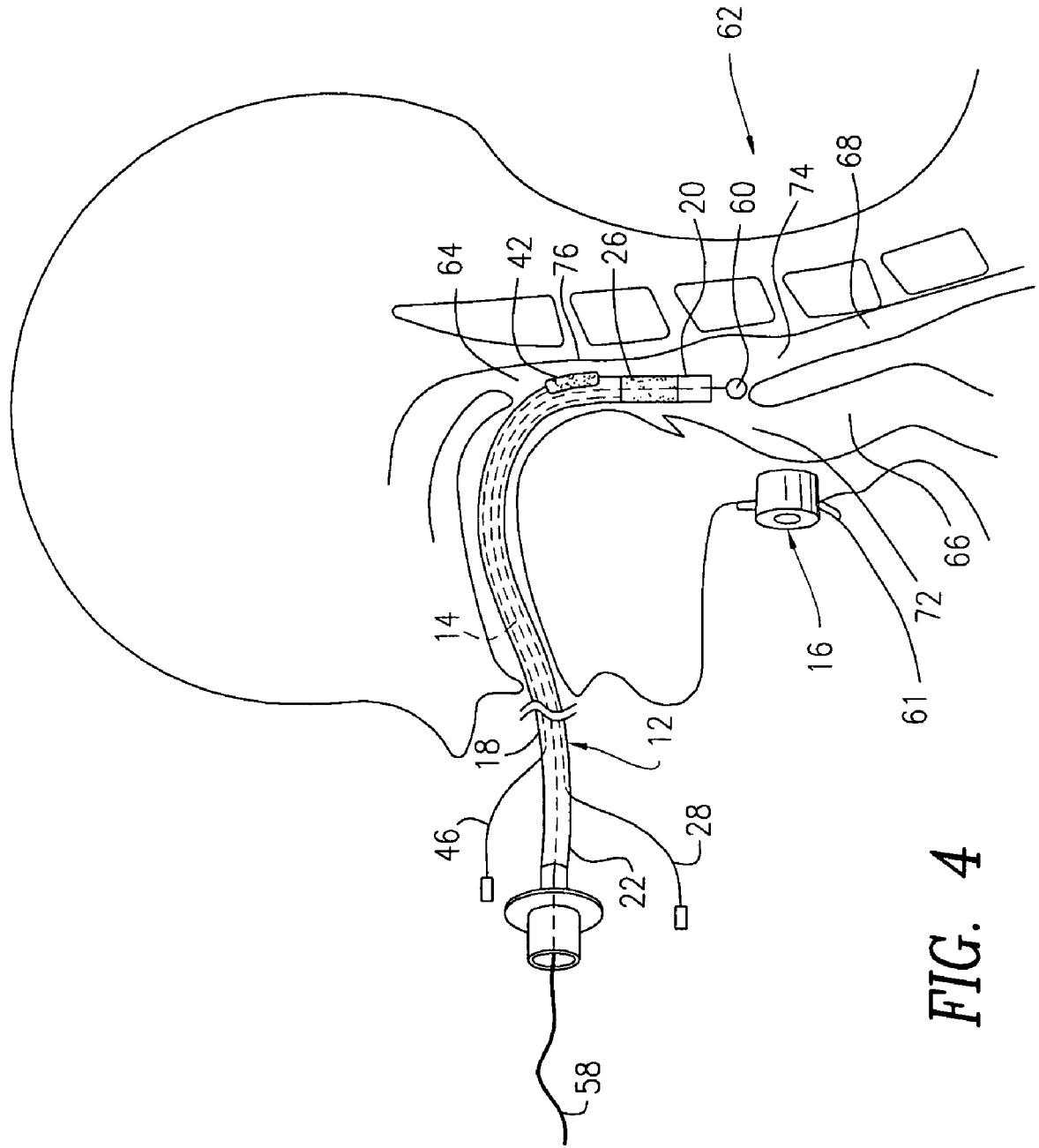
FIG. 4 is a schematic view similar to the view shown in FIG. 3, where the endotracheal tube and the metal stillette have been advanced into the oropharynx.
Figure 5:
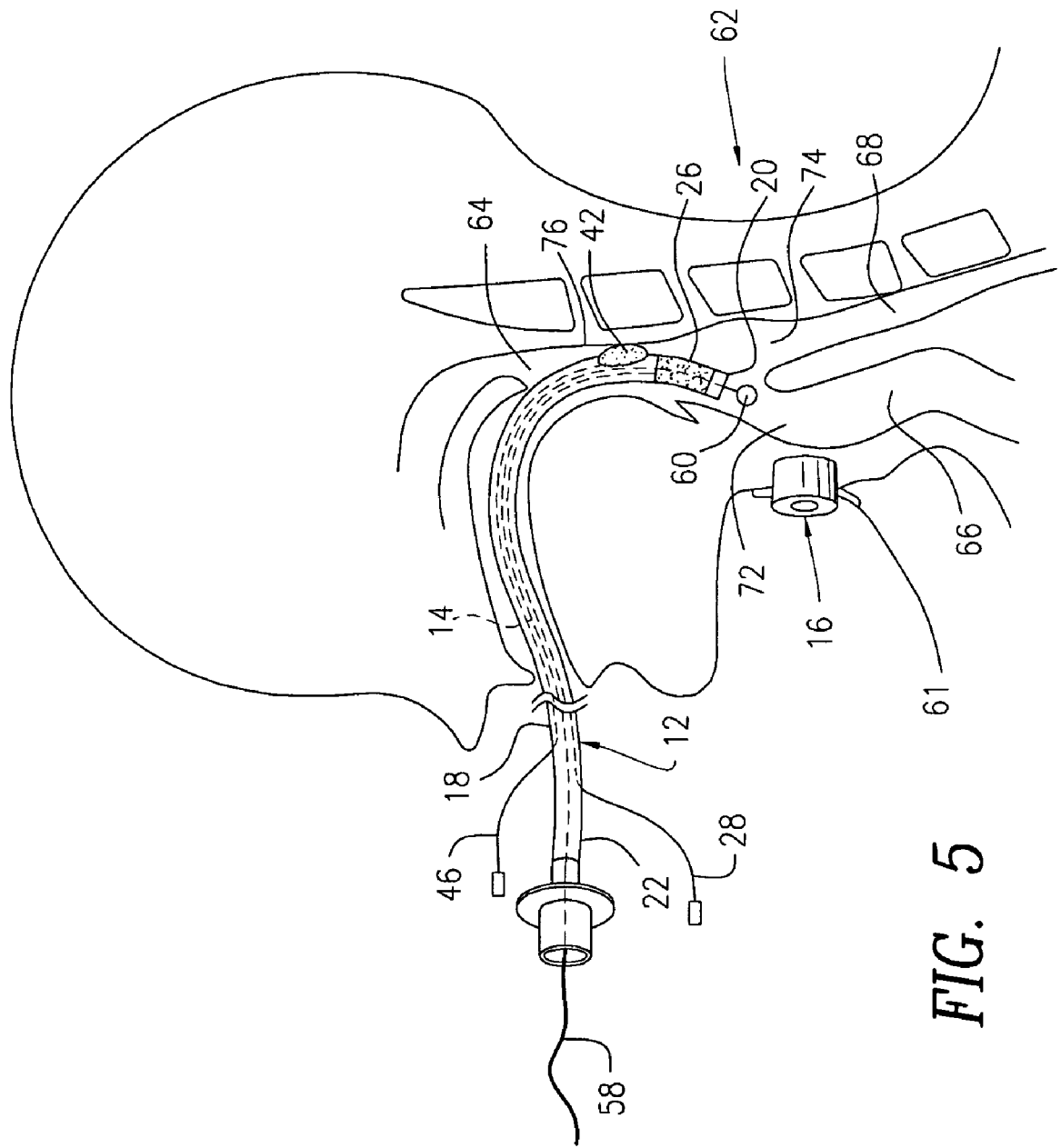
FIG. 5 is a schematic view similar to that of FIG. 4, where the second balloon has been inflated, causing the movement of the endotracheal tube and the metal stillette toward the inlet of the trachea.

The next steps, which are illustrated in FIGS. 3-7, involve the insertion of the endotracheal tube 12, along with the metal stillette 14 placed therein, into the throat 62. With reference to FIGS. 3 and 4, the endotracheal tube 12 is guided through the mouth 70 into the oropharynx 64. Note that in the foregoing step, the first and second balloons 26, 42 of the endotracheal tube 12 are both in their fully collapsed configuration in order to facilitate the insertion of the endotracheal tube 12 into the patient. In this position as shown in FIG. 4, the distal end 60 of the metal stillette 14 is located adjacent to the junction between the inlet 72 of the trachea 66 and the inlet 74 of the esophagus 68, while the second balloon 42 is in contact with the posterior wall 76 of the oropharynx 64. When the endotracheal tube 12 and the metal stillette 14 reach this position, the position is detected by the external guide system 16. Turning now to FIG. 5, the second balloon 42 is fully inflated, via the second inflating conduit 46, so as to assume its fully expanded configuration. As the second balloon 42 inflates, the contact between the second balloon 42 and the posterior wall 76 of the oropharynx 64 causes the endotracheal tube 12, along with the metal stillette 14 placed therein, to move in an anterior direction such that the distal end 20 of the tubular body 18 and the distal end 60 of the metal stillette 14 are urged toward the inlet 72 of the trachea and away from the inlet 74 of the esophagus 68.

The external guide system 16 can be used to align the metal stillette 14 toward the inlet 72 of the trachea 66 in the following manner. As previously indicated, the external guide system 16 senses the position of the metal stillette 14. The external guide system 16 may emit a signal that passes through the trachea 66 and receives a signal that can be presented in the form of an audio and/or visual signal, which is used to determine the position of the metal stillette 14. The intensity of the signal received by the external guide system 16 is indirectly proportional to the distance between the metal stillette 14 and the signal emitted by the external guide system 16; the intensity of the signal received by the external guide system 16 increases as the metal stillette 14 moves closer to the signal emitted by the external guide system 16. If the metal stillette 14 is properly aligned with the inlet 72 of the trachea 66, the intensity of the received audio signal will increase. This can be indicated by an audio or visual signal, which can appear on a display (not shown). If the metal stillette 14 is not properly aligned with the inlet 72 of the trachea 66 and is inadvertently advanced toward the esophagus 68, the intensity of the received audio signal will decrease or become nonexistent, and/or the visual signal may not appear on the display. The absence of an audio signal or a visual signal will indicate incorrect placement of the metal stillette 14, such as in the esophagus 68. If improperly placed, the metal stillette 14 can then be manually moved to achieve proper alignment with the trachea 66.

Figure 6:
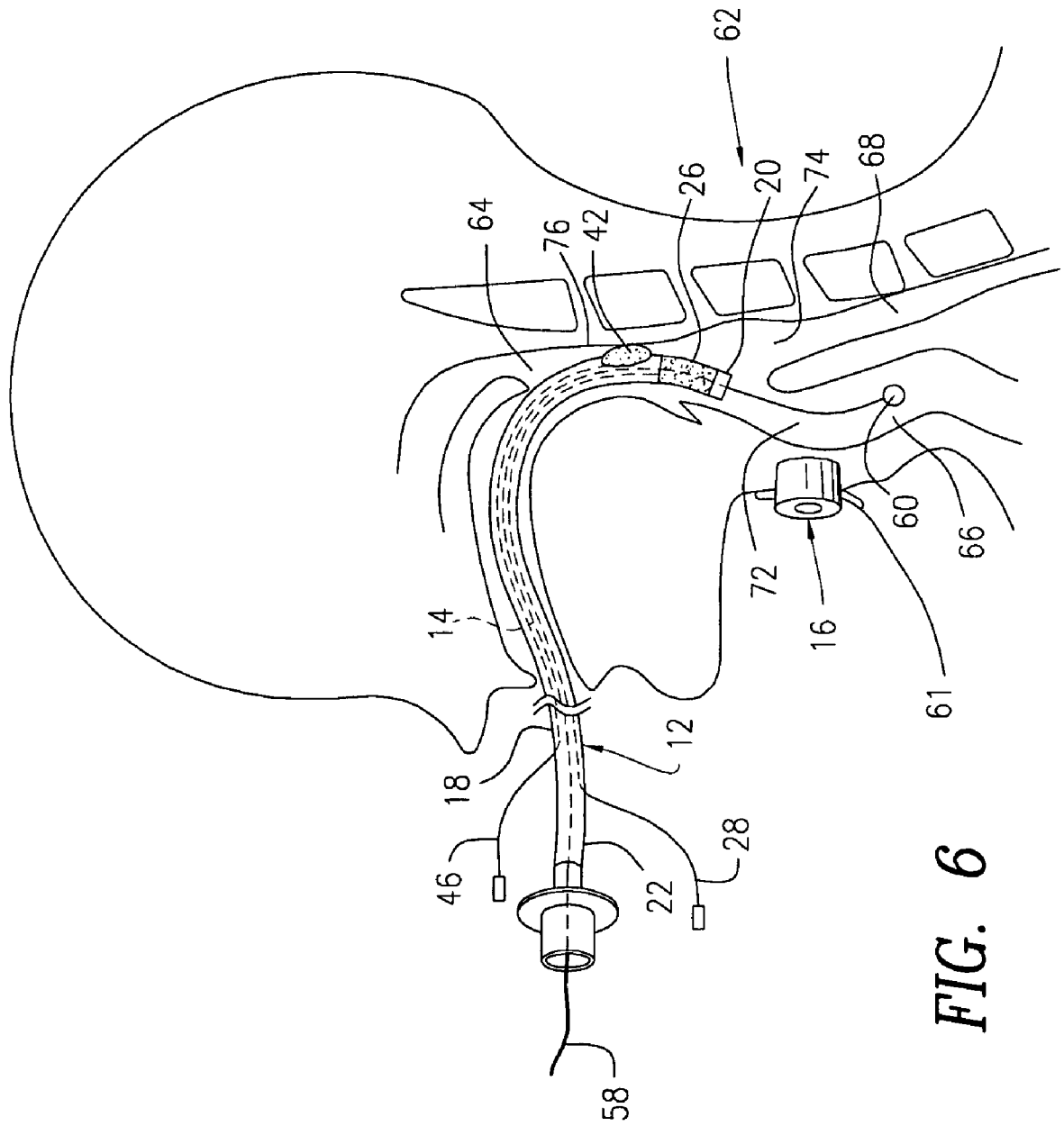
FIG. 6 is a schematic view similar to that of FIG. 5, where the metal stillette has been advanced into the trachea.
Figure 7:
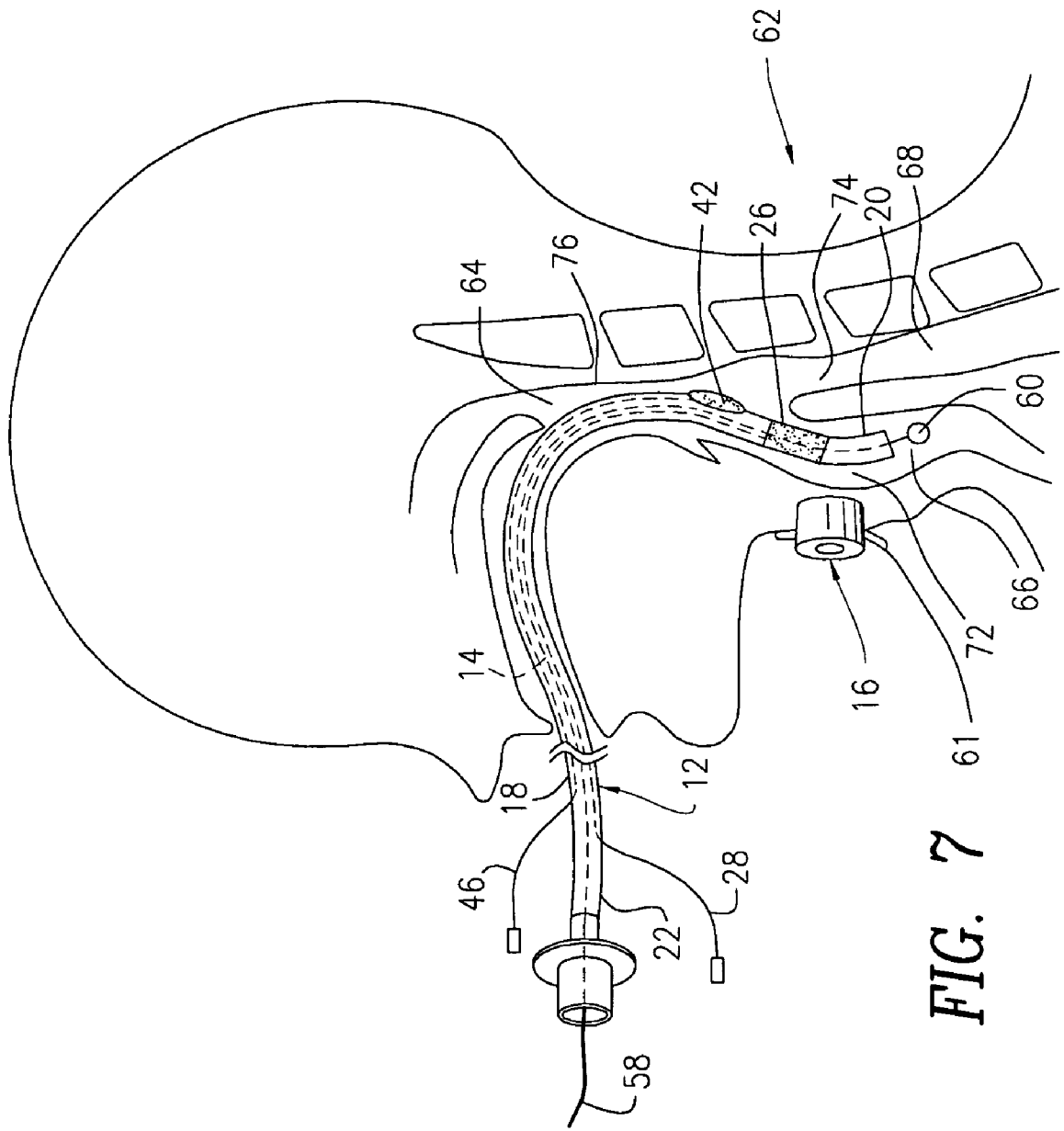
FIG. 7 is a schematic view similar to that of FIG. 6, where the second balloon has been collapsed, and the endotracheal tube has been advanced further into the trachea.
Figure 8:
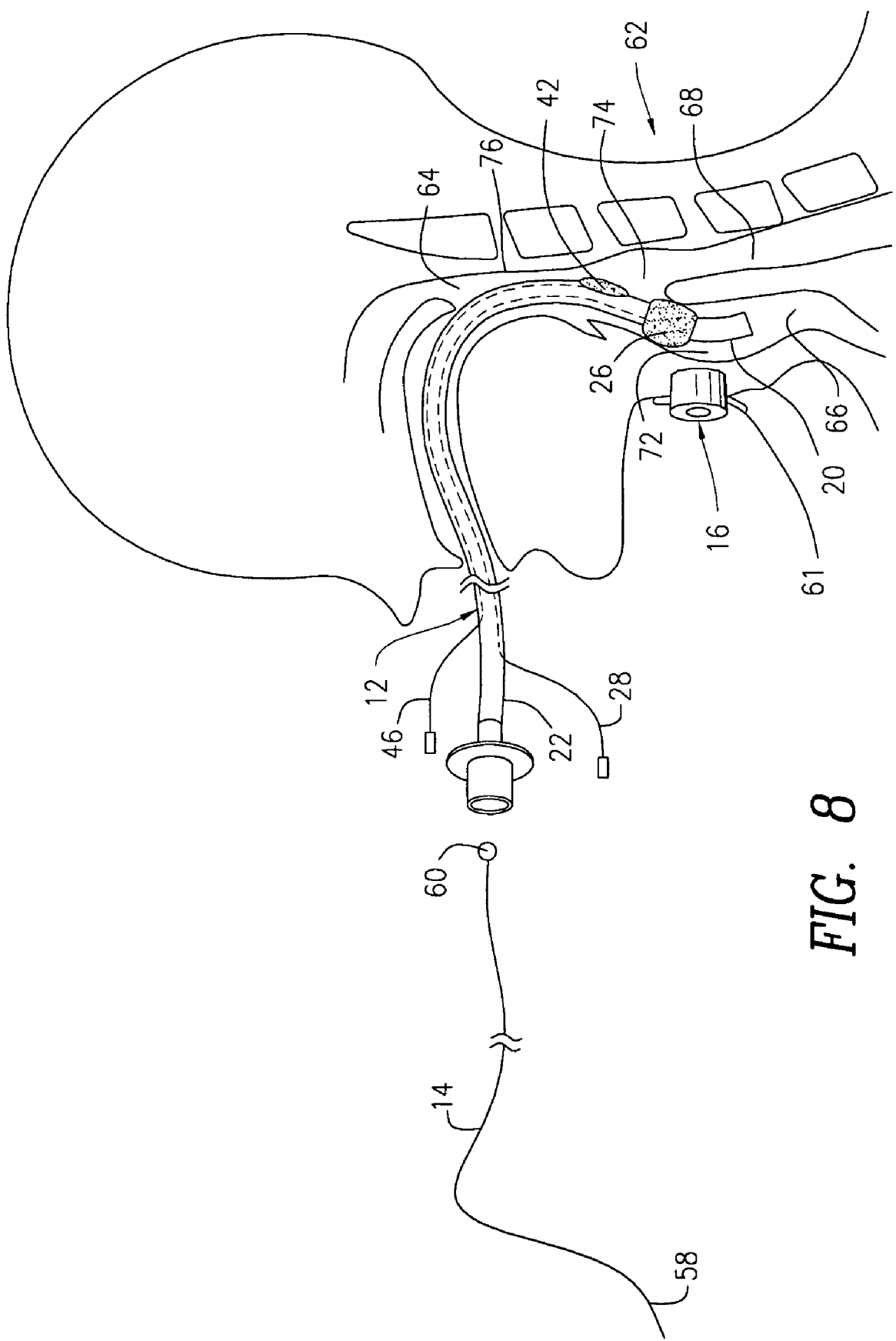
FIG. 8 is a schematic view similar to FIG. 7, where the metal stillette has been withdrawn from the patient and the first balloon has been inflated.

Once proper alignment between the metal stillette 14 and the inlet 72 of the trachea 66 has been achieved, the metal stillette 14 is manually pushed forward such that the distal end 60 of the metal stillette is advanced into the trachea 66 through the vocal cords, as shown in FIG. 6. The external guide system 16 can be used to confirm that the metal stillette 14 has been placed into the trachea 66. Once the metal stillette 14 is placed into the trachea 66, the second balloon 42 is deflated into its collapsed configuration. Turning now to FIG. 7, the endotracheal tube 12 is then pushed forward so as to advance toward the distal end 60 of the metal stillette 14, which is positioned in the trachea 66. Next, the metal stillette 14 is pulled out of the endotracheal tube 12 and withdrawn from the patient, as shown in FIG. 8. The first balloon 26 is inflated, via the first inflating conduit 28, so as to assume its fully expanded configuration. When expanded, the first balloon 26 serves to produce an air-tight seal in order to prevent upper airway obstruction and to prevent secretions from entering the lower tracheal regions.

It should be noted that numerous advantages are provided by the tracheal intubation device 10 of the present invention, and the above-described use of same to align the endotracheal tube 12 within the trachea 66. For example, the second balloon 42 is utilized to align the endotracheal tube 12 with the inlet 72 of the trachea 66. The external guide system 16 eliminates the need for a laryngoscope and the risks associated therewith. The metal stillette 42 provides rigidity to the endotracheal tube 12. Accordingly, the second balloon 42 and the external guide system 16 each simplify the complicated task of aligning the endotracheal tube 12 within the trachea 66. It should be understood that the present invention may be used to place the endotracheal tube 12 within the trachea 66 with the aid of the external guide system 16, without the need to use the second balloon 42. Likewise, the second balloon 42 can be used to move the endotracheal tube 12 toward the trachea 66, without the need to use the external guide system 16. The endotracheal tube 12 can even be placed in the trachea 66 without the need to use the metal stillette 14.

It will be understood that the embodiment described herein is merely exemplary and that a person skilled in the art may make many variations and modifications without departing from the spirit and scope of the invention. For example, fluid rather than air can be used to inflate the first and second balloons 26, 42. The second balloon 42 could even be replaced with a mechanical device that expands a dorsal area of the endotracheal tube 12 when actuated. The second balloon 42 may employ the use of markers (not shown), such as radio-opaque markers. All such variations and modifications are intended to be included within the scope of the invention as defined in the appended claims.

What is claimed is:

1. An endotracheal tube for insertion into a patient, comprising:
    a tubular body having a distal end;
    a primary cuff attached to said tubular body, said primary cuff being inflatable from a collapsed position to an expanded position; and
    a secondary cuff attached to said tubular body proximal to said primary cuff, said secondary cuff being inflatable from a collapsed position to an expanded position,
    whereby when the endotracheal tube is inserted into a patient's body, inflating said secondary cuff moves the endotracheal tube in an anterior direction toward the inlet of a patient's trachea.

2. The endotracheal tube of claim 1, wherein said tubular body includes a dorsal section and has a circumference, and wherein said secondary cuff is attached to said dorsal section of said tubular body and covers approximately half of said circumference of said tubular body.

3. The endotracheal tube of claim 2, wherein said primary cuff is a first inflatable balloon, and wherein said secondary cuff is a second inflatable balloon.

4. The endotracheal tube of claim 3, wherein said tubular body includes a first channel sized so as to allow air to pass through said first channel and a second channel sized so as to allow air to pass through said second channel.

5. The endotracheal tube of claim 4, wherein said first balloon is inflatable to its said expanded position when air is passed through said first channel, and wherein said second balloon is inflatable to its said expanded position when air is passed through said second channel.

6. A tracheal intubation device, comprising:
    a endotracheal tube for insertion into a patient's body, said endotracheal tube including a tubular body, a primary cuff attached to said tubular body, said primary cuff being inflatable from a collapsed position to an expanded position, a secondary cuff attached to said tubular body proximal to said primary cuff, said secondary cuff being inflatable from a collapsed position to an expanded position;
    a stillette removably positioned within said tubular body; and
    guiding means for guiding said stillette and said endotracheal tube within a patent's body, said guiding means positioned external to a patient and sized and shaped so as to transmit a signal and to receive a signal indicating the location of said stillette in a patient's body.

7. The tracheal intubation device of claim 6, wherein the intensity of the signal received by said guiding means increases as said stillette moves closer to the signal emitted by said guiding means.

8. The tracheal intubation device of claim 7, wherein, when said endotracheal tube is inserted in a patient's body, the signal received by said guiding means increases as said endotracheal tube and said stillette move toward the trachea.

9. The tracheal intubation device of claim 8, wherein, when said endotracheal tube is inserted in a patient's body, the signal received by said guiding means decreases as said endotracheal tube and said stillette move toward the esophagus.

10. The tracheal intubation device of claim 8, wherein, when said endotracheal tube is inserted in a patient's body, the signal received by said guiding means becomes nonexistent as said endotracheal tube and said stillette move toward the esophagus.

11. The tracheal intubation device of claim 6, wherein, when said endotracheal tube is inserted in a patient's body, inflating said secondary cuff moves said endotracheal tube in an anterior direction toward the inlet of a patient's trachea.

12. The tracheal intubation device of claim 11, wherein said tubular body includes a dorsal section and has a circumference, and wherein said secondary cuff is attached to said dorsal section of said tubular body and covers approximately half of said circumference of said tubular body.

13. The tracheal intubation device of claim 6, wherein said endotracheal tube is movable relative to said stillette such that after said stillette is positioned in the trachea, said endotracheal tube can be moved along said stillette to place said endotracheal tube in the trachea.

14. The guiding system of claim 6, wherein the endotracheal tube is movable relative to said stillette such that after said stillette is positioned in the trachea, the endotracheal tube can be moved along said stillette to place the endotracheal tube in the trachea.

15. A method for positioning an endotracheal tube, having a primary cuff and a secondary cuff, within a patient's body, comprising the steps of:
- (a) inserting the endotracheal tube in a patient's body until a distal end of the endotracheal tube is positioned adjacent to the junction of the trachea and the esophagus;
- (b) urging the endotracheal tube in an anterior direction toward the inlet of the trachea, comprising inflating the second cuff so as to move the endotracheal tube in an anterior direction toward the inlet of the trachea; and
- (c) continually inserting the endotracheal tube until the distal end of the endotracheal tube is positioned within the trachea.

16. The method of claim 15, further comprising the steps of transmitting a signal toward the trachea and receiving a signal indicating the location of the endotracheal tube.

17. The method of claim 16, wherein the signal transmitted substantially avoids encompassing the esophagus.

* * * * *